United States Patent [19]

Holtermann et al.

[11] Patent Number: 5,149,894
[45] Date of Patent: Sep. 22, 1992

[54] ALKYLATION USING ZEOLITE SSZ-25

[75] Inventors: Dennis L. Holtermann, Crockett; Robert A. Innes, San Rafael, both of Calif.

[73] Assignee: Chevron Research and Technology Company, San Francisco, Calif.

[21] Appl. No.: 745,582

[22] Filed: Aug. 15, 1991

Related U.S. Application Data

[60] Continuation-in-part of Ser. No. 697,519, Apr. 29, 1991, and Ser. No. 333,666, Apr. 5, 1989, abandoned, which is a division of Ser. No. 14,958, Feb. 17, 1987, Pat. No. 4,826,667, which is a continuation-in-part of Ser. No. 823,698, Jan. 29, 1986, abandoned, said Ser. No. 697,519, is a continuation of Ser. No. 595,084, Oct. 10, 1990, abandoned.

[51] Int. Cl.$^5$ .............................................. C07C 2/66
[52] U.S. Cl. ...................................... 585/467; 423/326
[58] Field of Search ......................................... 585/467

[56] References Cited

U.S. PATENT DOCUMENTS

| | | | |
|---|---|---|---|
| 4,826,667 | 5/1989 | Zones et al. | 423/326 |
| 4,891,458 | 1/1990 | Innes et al. | 585/323 |
| 4,950,823 | 8/1990 | Harandi et al. | 585/467 |
| 4,954,325 | 9/1990 | Rubin | 423/328 |
| 4,992,606 | 2/1991 | Kushnerick et al. | 585/467 |

OTHER PUBLICATIONS

Soc Npra/paper/AM-88-44 "Alkylation of FCC off Gas Olefins with Aromatics Via Catalytic Distillation" by Elwyn E. Partin, Mar. 22, 1988, 7 Pages.
Journal Catalysis, vol. 109, pp. 212-216, (1988) W. W. Kaeding et al.

*Primary Examiner*—Asok Pal
*Assistant Examiner*—Achutamurthy P.
*Attorney, Agent, or Firm*—Witta Priester; Thomas G. DeJonghe

[57] ABSTRACT

A process for the alkylation of an aromatic hydrocarbon which comprises contacting the aromatic hydrocarbon with a $C_2$ to $C_4$ olefin alkylating agent under at least partial liquid phase conditions, and in the presence of a catalyst comprising zeolite SSZ-25. The invention also provides a process for producing a reduced benzene content gasoline blend stock. A benzene-containing light hydrocarbon stream having less than 50 weight present benzene is contacted with a $C_2$-$C_4$ olefin stream in an alkylation zone containing an SSZ-25 catalyst under alkylation conditions to produce an alkylated light hydrocarbon stream with reduced benzene content. The alkylated light hydrocarbon stream is then usable as gasoline blend stock.

54 Claims, 2 Drawing Sheets

FIG_1

FIG_2

5,149,894

ALKYLATION USING ZEOLITE SSZ-25

This application is a continuation-in-part of application Ser. No. 333,666, filed Apr. 5, 1989, now abandoned, which is in turn a divisional of application Ser. No. 14,958, filed Feb. 17, 1987, now U.S. Pat. No. 4,826,667, which is in turn a continuation-in-part of Ser. No. 823,698, filed Jan. 29, 1986, now abandoned. This application is also a continuation-in-part of application Ser. No. 697,519 filed Apr. 29, 1991, which is in turn a continuation of Ser. No. 595,084 filed Oct. 10, 1990, now abandoned.

FIELD OF THE INVENTION

The present invention relates to the reaction of alkylating. In one embodiment the invention relates to a process for preparing monoalkylated aromatic compounds by subjecting an aromatic hydrocarbon to alkylation with a $C_2$ to $C_4$ olefin, under at least partial liquid phase conditions, utilizing zeolite SSZ-25 as the alkylation catalyst. In another embodiment, the present invention relates to a process for removing benzene from refinery streams by particularly efficient catalytic alkylation.

BACKGROUND OF THE INVENTION

Most industrial processes for the alkylation of aromatic hydrocarbons employ a Friedel-Crafts type of catalyst such as aluminum chloride, boron trifluoride, hydrofluoric acid, liquid and solid phosphoric acid, sulfuric acid and the like. These materials are highly corrosive to process equipment, cause many operational problems, and are often difficult to dispose of in an environmentally acceptable manner.

It has long been a goal of research to find noncorrosive, solid catalysts to replace the Friedel-Crafts catalysts. To this end, various types of zeolite catalysts have been proposed.

U.S. Pat. No. 4,891,458 to Innes et al. discloses a process for the alkylation of an aromatic hydrocarbon which comprises contacting the aromatic hydrocarbon with a $C_{2\ to\ C_4}$ olefin alkylating agent, under at least partial liquid phase conditions, and in the presence of a catalyst comprising zeolite beta.

U.S. Pat. No. 4,954,325 to Rubin et al. discloses a synthetic porous crystalline material with X-ray diffraction lines similar to SSZ-25. This patent discloses 16 different utilities for this material. Included among these is the suggestion that this material effectively catalyzes the alkylation of aromatic hydrocarbons with gaseous olefins to provide short chain alkyl aromatics, such as cumene (See Col 6, lines 49-56.) Disclosed reaction condition range from 10° C. to 125° C. (50° F. to 252° F.).

Despite the available literature on zeolite catalysis and the recognized advantages of using a noncorrosive catalyst, zeolites are not always the preferred catalysts for use in industrial alkylation processes. Under commercially realistic conditions, many of the zeolite catalysts described in the literature have tended to deactivate rapidly due to fouling, produced the desired product in a lower yield than the competing Friedel-Crafts catalyst, or made a product which failed to meet established purity specifications.

Although some of the zeolites described in the art may be useful for commercial alkylation processes, the art is currently unpredictable with regard to whether a zeolite catalyst will perform effectively for production of ethyl benzene and/or cumene.

On a related front, the requirement that lead be phased out of gasoline and the introduction of premium unleaded gasoline has created a strong demand for increased gasoline octane numbers. Conventional approaches such as increasing operating severity in reformers and fluid catalytic cracking units, or using octane catalysts or additives in the fluid catalytic cracking (FCC) result in losses of gasoline yield. In addition, these approaches often increase the fuel gas yields in a refinery which may sometimes cause a reduction in refinery throughput and profitability. Also, these approaches often result in increased benzene content in the gasoline.

Typical gasoline contains 1 to 5 liquid volume percent benzene, a chemical which has a high octane blending value, but is considered environmentally hazardous. The State of California, for example, has included benzene in its toxic chemicals list, and the State of California Air Resources Board and the United States Environmental Protection Agency are considering regulations to limit the amount of benzene which may be present in gasoline. It is anticipated that a pending change in the Clean Air Act will also limit the allowable percent of total. It is therefore highly desirable to remove benzene from gasoline blend stocks.

Physically separating benzene from gasoline by solvent extraction has the undesirable effect of decreasing both the octane rating and the volume of gasoline.

As an alternative, benzene in gasoline blend stocks may be hydrogenated to a nonaromatic compound. This approach is also undesirable, however, because it requires a relatively high pressure operation and consumes hydrogen which is usually expensive in a refinery. Hydrogenation of benzene also reduces the octane rating of the gasoline.

To overcome these disadvantages, it has been found that benzene may be alkylated with resulting actual improvements in both the octane and the volume of gasoline produced. Co-pending U.S. patent application Ser. No. 64,121, filed Oct. 28, 1988, discloses reacting a refinery stream with an olefin-containing stream in a distillation column reactor in the presence of an alkylation catalyst (beta zeolite) to thereby alkylate light aromatics, particularly benzene.

The chemical reactions involving alkylation of aromatics with olefins are well known. For example, U.S. Pat. No. 2,860,173 discloses the use of solid phosphoric acid (SPA) as a catalyst for the alkylation of benzene with propylene to produce cumene. U.S. Pat. No. 4,347,393 discloses the use of Freidel Crafts catalyst, especially aluminum chloride for this reaction. More recently, certain rare earth modified zeolites and Mobil's HZSM-5 zeolite catalyst have been used to carry out this reaction. Examples may be found in the *Journal Catalysis* Volume 109, pages 212-216 (1988). Similarly, the alkylation of benzene with ethylene to produce ethylbenzene is a well known commercial process. The Mobil/Badger ethylbenzene process produces high purity ethylbenzene in vapor phase with a multiple-bed reactor and a series of distillation columns. A description of the process using a dilute ethylene stream may be found in the *Oil and Gas Journal,* Volume 7, pages 58-61 (1977).

A paper entitled "Alkylation of FCC Off Gas Olefins with Aromatics Via Catalytic Distillation", by I. E. Partin was presented at the National Petroleum Refineries Association Meeting, Mar. 22, 1988. This paper discloses a catalytic distillation process which uses the refiners light olefin gases such as ethylene and propylene, present in FCC and coker unit tail gas to alkylate light aromatics such as benzene and toluene, present in reformate. In the process as taught in this paper full range reformate is charged to the lower distillation section and the total FCC off gas stream is charged beneath the catalyst section. The solid proprietary catalyst is secured within supports which form bundles for installation in the distillation tower. As olefins and aromatics proceed into the catalyst section and react, the heavier alkylated aromatics move down out into the lower fractionation section and out the bottom of the tower with the bulk of the reformate. Light components, including light gases, proceed up the reactor and are stripped out in the upper distillation section. Part of the unreacted benzene is recycled back to the tower to increase benzene conversion. Noncondensible gases go to fuel and light liquid is circulated back to the refinery gas plants or to gasoline blending.

It is important to distinguish that while catalytic aromatic alkylation is known, it is subject to the unexpected and unpredictable vagaries of catalytic processes. For example, in U.S. Pat. No. 3,527,823 (Jones) there is disclosed the reaction of benzene and propylene over phosphoric acid catalyst in a nondistilling upflow reactor to produce cumene. While the benzene-propylene reaction was successful, the Jones process was not applicable to the reaction of benzene and ethylene (Column 13, line 36 of Jones). Poor yields of ethyl benzene were obtained. However, increasing ethylene purity increased the conversion of ethylene (Column 13, line 10 of Jones) although the yield of ethyl benzene was still not satisfactory. In another U.S. Pat. No. 3,437,705, Jones discloses the alkylation of an aromatic compound in a process operating with an aromatic to olefin mole ratio of from 2:1 to 30:1. The process is characterized by the presence of an unreacted vapor diluent, such as propane, in the reaction zone. The total alkylation effluent is passed to a flash distillation zone where the unreacted diluent is separated. The process is purportedly applicable to a variety of reactions using feedstocks containing unreactive vapor diluents.

Another point to be kept in mind is that operation in a nondistilling reactor system is significantly different from operation in the alkylation zone of a distillation reactor. In the former, in the alkylation zone the reactants and the products of reaction remain in contact with the catalyst throughout the process. As a result, the products can be adsorbed by the catalyst and thereby shield it from the reactants. Also, back reaction can occur towards an equilibrium state. In the latter, i.e., in the distillation zone whereat alkylation is occurring, the products are constantly stripped from the catalyst bed and the benzene is refluxed back into the bed, whereby back reaction is eliminated or at least virtually eliminated. Also, since there is no competition for catalytic sites, the reaction can proceed at a faster pace and/or towards a different product mix. Some catalysts work well in both environments, others in one but not the other. A single catalyst which could be used in either environment would be useful in that a refinery carrying out alkylation of aromatics using both types of alkylation zones would only need to maintain supplies of a single catalyst.

It should also be recognized that such reactions as the conversion of benzene to produce high purity cumene via alkylation are carried out under much different reaction conditions than is the reaction of a refinery stream having only a limited amount of benzene along with numerous other hydrocarbons with olefins to form a low benzene content gasoline blend stock. In the former instance one operates with an excess, often a great excess, of the benzene as compared to the olefin. For example, olefin to benzene mole ratios of 1:4 to 1:30 are common for such reactions. By contrast, the olefin to benzene mole ratio for producing a refinery stream having only a limited amount of benzene from a refinery stream having several percent benzene would generally be above 0.5:1 and might commonly fall within the range from about 0.5:1 to about 5:1 or even 10:1. Thus, the fact that a particular catalyst might be usable and practical for cumene production does not mean that the same catalyst will be useful for reducing the benzene content of a refinery stream.

In one aspect, the present invention overcomes the disadvantages of the prior art in that extremely efficient alkylation of the benzene in a refinery stream is accomplished generally over 60% conversion, and even up to 90% or more conversion, utilizing a specific catalyst and specific process conditions when carrying out the alkylation.

SUMMARY OF THE INVENTION

The present invention provides a hydrocarbon conversion process comprising using calcined SSZ-25 zeolite under hydrocarbon conversion conditions in the reaction of alkylating wherein said calcined SSZ-25 zeolite has the X-ray diffraction lines shown in Table 2 below.

In one embodiment, the present invention provides a process for the alkylation of an aromatic hydrocarbon which comprises contacting the aromatic hydrocarbon with a $C_2$ to $C_4$ olefin alkylating agent under at least partial liquid phase conditions, and in the presence of a catalyst comprising zeolite SSZ-25.

Among other factors, the present invention is based on the discovery that aromatic hydrocarbons, such as benzene, toluene or xylene, can be effectively alkylated with lower ($C_2$-$C_4$) olefins using a zeolite SSZ-25 catalyst which provides monoalkylated products in high yield and high product purity. Surprisingly, the zeolite SSZ-25 catalyst is able to provide high yields of monoalkylated product for much longer periods of time than other zeolite catalysts. Furthermore, SSZ-25 is able to operate for long periods at lower benzene to olefin ratios than other zeolites. As a result, energy and capital savings may be obtained by reducing the benzene recycle ratio. Another unusual feature of alkylating using SSZ-25 is that the di-isopropylbenzene by-product stream consists mainly of the 1,4-isomer rather than the 1,3-isomer. The 1,4-isomer can be sold as a feedstock for the production of hydroquinone.

In a further embodiment of the present invention, monoalkylated aromatic hydrocarbons are prepared in high yield by combining alkylation and transalkylation in a process which comprises:

(a) contacting a stoichiometric excess of an aromatic hydrocarbon feed with a $C_2$ to $C_4$ olefin in an alkylation zone under at least partial liquid phase conditions and in the presence of a catalyst comprising zeolite SSZ-25;

(b) separating the product from step (a) into fractions comprising (1) an aromatic hydrocarbon fraction, (2) a monoalkyl aromatic hydrocarbon fraction and (3) a polyalkyl aromatic hydrocarbon fraction; and (c) contacting the polyalkyl aromatic hydrocarbon fraction with additional aromatic hydrocarbon feed in a transalkylation zone under at least partial liquid phase conditions and in the presence of a transalkylation catalyst, such as zeolite beta or zeolite Y.

Another embodiment of the present invention is a process for alkylating an aromatic hydrocarbon by reacting an aromatic hydrocarbon and a $C_2$ to $C_4$ olefin in the presence of a calcined SSZ-25 alkylation catalyst, said process comprising introducing a mixture of aromatic hydrocarbon and $C_2$ to $C_4$ olefin into the first stage of an alkylator having at least two reactor stages, each stage containing alkylation catalyst, and mixing the effluent from each reactor stage with fresh mixture of aromatic hydrocarbon and $C_2$ to $C_4$ olefin prior to introduction of said effluent to the next reactor stage, wherein the alkylation catalyst in at least one of the reactor stages if SSZ-25. Preferably the alkylation catalyst in all of the reactor stages is SSZ-25.

In another embodiment of the present invention, all reactor stages have about the same inlet temperature and outlet temperature. The temperature balance is achieved by careful adjustment of the ratio of aromatics and olefin added between stages. In yet another embodiment of the present invention, the ratio of aromatic hydrocarbon to $C_2$ to $C_4$ olefin introduced into each reactor stage is sufficiently high to achieve an acceptable run length of at least one month, preferably at least one year. In a further embodiment of this invention each of the reactor stages is adiabatic.

In accordance with an embodiment of the invention a process is set forth for contacting a benzene-containing light hydrocarbon stream having less than 50 weight percent benzene with a $C_2$-$C_4$ olefin stream in an alkylation zone containing an SSZ-25 zeolite catalyst under alkylation conditions to produce an alkylated light hydrocarbon stream with reduced benzene content. The alkylated light hydrocarbon stream is then usable as a gasoline blend stock.

Alkylation of a refinery stream derived from a typical reformate, such as a light reformate fraction, with a $C_2$-$C_4$ olefin-containing stream, preferably a $C_3$ olefin containing stream, utilizing an SSZ-25 zeolite catalyst in accordance with the present invention leads to a conversion of a high proportion of the benzene to alkylated benzene. Up to about 90% conversion of the benzene is attainable depending on the olefin/benzene ratio. If desired, any remaining nonalkylated benzene can be separated and recycled to the alkylation reactor or hydrogenated to substantially eliminate benzene. Furthermore, alkylation using the SSZ-25 catalyst can be efficiently carried out using either a distilling reaction zone or a nondistilling reaction zone.

BRIEF DESCRIPTION OF THE DRAWINGS

The invention will be better understood by reference to the figures wherein.

DETAILED DESCRIPTION OF THE INVENTION

Zeolite SSZ-25 is a synthetic crystalline aluminosilicate described in U.S. Pat. No. 4,826,667, which is incorporated herein by reference in its entirety for further details on this zeolite, its preparation and properties. SSZ-25 zeolites, as synthesized, have a crystalline structure whose X-ray powder diffraction pattern shows the following characteristic lines:

TABLE 1

| $2\theta$ | d/n | $I/I_o$ |
|---|---|---|
| 3.05 | 29.0 | 20 |
| 6.42 | 13.77 | 100 |
| 7.18 | 12.31 | 100 |
| 7.88 | 11.22 | 47 |
| 9.62 | 9.19 | 53 |
| 15.75 | 5.63 | 27 |
| 19.37 | 4.58 | 47 |
| 22.57 | 3.94 | 50 |
| 23.05 | 3.86 | 30 |
| 26.03 | 3.42 | 73 |
| 26.85 | 3.32 | 33 |

The X-ray powder diffraction patterns were determined by standard techniques. The radiation was the K-alpha/doublet of copper and a scintillation counter spectrometer with a strip chart pen recorder was used to record the diffracted X-rays. The peak heights I and the positions, as a function of $2\theta$, where $\theta$ is the Bragg angle, were read from the spectrometer chart. From these measured values, the relative intensities, 100 $I/I_o$, where $I_o$ is the intensity of the strongest line or peak, and d, the interplanar spacing in Angstroms corresponding to the recorded lines, can be calculated. The X-ray diffraction pattern of Table 1 is characteristic of SSZ-25 zeolite. The zeolite produced by exchanging the metal or other cations present in the zeolite with various other cations yields substantially the same diffraction pattern although there can be minor shifts in interplanar spacing and minor variations in relative intensities. Minor variations in the diffraction pattern can also result from variations in the silica-to-alumina mole ratio from sample to sample. Calcination can also cause minor shifts in the X-ray diffraction pattern. Notwithstanding these minor perturbations, the basic crystal lattice structure remains unchanged. Variations in the diffraction pattern often do result from variations in the templating compound used.

After calcination the SSZ-25 zeolite has a crystalline structure whose X-ray powder diffraction pattern shows the following characteristic lines as indicated in Table 2.

TABLE 2

| $2\theta$ | d/n | $I/I_o$ |
|---|---|---|
| 3.4 | 25.5 | 17 |
| 7.19 | 12.30 | 100 |
| 8.04 | 11.00 | 55 |
| 10.06 | 8.78 | 63 |
| 14.35 | 6.17 | 40 |
| 16.06 | 5.51 | 17 |
| 22.77 | 3.90 | 38 |
| 23.80 | 3.74 | 20 |
| 26.08 | 3.417 | 65 |

The calcined form is used for alkylation.

SSZ-25 has a mole ratio of an oxide selected from silicon oxide, germanium oxide, and mixtures thereof to an oxide selected from aluminum oxide, gallium oxide, iron oxide, boron oxide and mixtures thereof in the range of 10 to 200, and having the X-ray diffraction lines of Table 2 above. The zeolite further has a composition, as synthesized and in the anhydrous state, in terms of mole ratios of oxides as follows: (0.1 to 2.0)(Q$_2$O:(0.1 to 2.0)M$_2$O:W$_2$O$_3$:(10 to 200)YO$_2$ wherein M is an alkali metal cation, W is selected from aluminum, gallium, iron, boron and mixtures thereof, Y is selected from silicon, germanium and mixtures thereof, and Q is an adamantane quaternary ammonium ion. SSZ-25 zeolites can have a YO$_2$:W$_{2/O3}$ mole ratio in the range of 10 to 200. As prepared, the silica:alumina mole ratio is typically in the range of 10:1 to about 200:1. Higher mole ratios can be obtained by treating the zeolite with chelating agents or acids to extract aluminum from the zeolite lattice. The silica:alumina mole ratio can also be increased by using silicon and carbon halides and other similar compounds. Preferably, SSZ-25 is an aluminosilicate wherein W is aluminum and Y is silicon. Preferably, the silica to alumina mole ratio is between 10:1 and 50:1, more preferably between 15:1 and 40:1. It is preferred to use SSZ-25 zeolites with low silica to alumina ratios for the alkylation processes of this invention.

One method of preparing SSZ-25 zeolites comprises preparing an aqueous mixture containing sources of an adamantane quaternary ammonium ion, an oxide selected from aluminum oxide, gallium oxide, iron oxide, boron oxide and mixtures thereof, and an oxide selected from silicon oxide, germanium oxide, and mixtures thereof, and having a composition, in terms of mole ratios of oxides, falling within the following ranges: YO$_2$/W$_2$O$_3$, 10:1 to 200:1; and Q$_2$O/YO$_2$ 0.15:1 to 0.50:1; wherein Y is selected from silicon, germanium, and mixtures thereof, W is selected from aluminum, gallium, iron, boron and mixtures thereof, and Q is an adamantane quaternary ammonium ion; maintaining the mixture at a temperature of at least 100° C. until the crystals of said zeolite are formed; and recovering said crystals.

The reaction mixture should have a composition in terms of mole ratios falling within the following ranges:

|  | Broad | Preferred |
|---|---|---|
| YO$_2$/W$_2$O$_3$ | 10–200 | 30–100 |
| OH/YO$_2$ | 0.1–1.0 | 0.20–0.40 |
| Q/YO$_2$ | 0.15–0.50 | 0.15–0.30 |
| M$^+$/YO$_2$ | 0.05–0.30 | 0.15–0.30 |
| H$_2$O/YO$_2$ | 2.0–300 | 35–60 |
| Q/Q + M$^+$ | 0.30–0.70 | 0.40–0.67 | wherein Q is an adamantane quaternary ammonium ion, Y is silicon, germanium or both, and W is aluminum, gallium, iron, boron or mixtures thereof. M is an alkali metal, preferably sodium or potassium. The organic adamantane compound which acts as a source of the adamantane quaternary ammonium ion employed can provide a hydroxide ion.

When using the adamantane quaternary ammonium hydroxide compound as a template, it has been found that purer forms of SSZ-25 are prepared when there is an excess of the adamantane quaternary ammonium hydroxide compound present relative to the amount of alkali metal hydroxide and that when the OH$^-$/SiO$_2$ molar ratio is greater than 0.40, then M$^+$/SiO$_2$ molar ratio should be less than 0.20.

M is typically a sodium ion from the original synthesis but may also be a metal ion added by ion exchange techniques. Suitable metal ions include those from Groups IA, IIA or IIIA of the Periodic Table or transition metal. Examples of such ions include ions of lithium, potassium, calcium, magnesium, barium, lanthanum, cerium, nickel, platinum, palladium, and the like.

Another method of preparing SSZ-25 zeolites, comprises preparing an aqueous mixture containing a minor quantity of either an adamantane quaternary amine ion, such as N,N,N-trimethyl-2-adamantammonium hydroxide, or a polar adamantyl derivative, such as 1-adamantanol or an adamantane amine, a larger quantity of at least one small aliphatic or cycloaliphatic amine ranging from 1 to 8 carbons, such as piperidine, and preferably seeds of SSZ-25 zeolite. The mixture is maintained at a temperature of at least 100° C. until the crystals are formed.

The resulting, as synthesized zeolite, in the anhydrous state, has a composition in terms of mole ratios of oxides as follows: (0.1 to 2.0)Q$_2$O:(0.1 to 2.0)M$_2$O:W$_2$O$_3$:(10 to 200)YO$_2$, wherein M is an alkali metal cation; W is selected from aluminum, gallium, iron, boron, and mixtures thereof; Y is selected from silicon, germanium, and mixtures thereof; and Q is either a mixture of an adamantane quaternary ammonium ion and an amine mixture, or is a mixture of a polar adamantane derivative and an amine mixture.

For high catalytic activity, the zeolite SSZ-25 should be predominantly in its hydrogen ion form. Generally, the zeolite is converted to its hydrogen form by ammonium exchange followed by calcination. If the zeolite is synthesized with a high enough ratio of organonitrogen cation to sodium ion, calcination alone may be sufficient. It is preferred that, after calcination, a major portion of the cation sites are occupied by hydrogen ions and/or rare earth ions. It is especially preferred that at least 80% of the cation sites are occupied by hydrogen ions and/or rare earth ions, preferably hydrogen ions.

The pure zeolite may be used as a catalyst, but generally it is preferred to mix the zeolite powder with an inorganic oxide binder such as alumina, silica, silica/alumina, or naturally occurring clays and form the mixture into tablets or extrudates. The final catalyst may contain from 1 to 99 wt. % zeolite SSZ-25. Usually the zeolite SSZ-25 content will range from 10 to 90 wt. %, and more typically from 60 to 80 wt. %. A preferred inorganic binder is alumina. The mixture may be formed into tablets or extrudates having the desired shape by methods well known in the art. The extrudates or tablets will usually be cylindrical in shape. Other shapes with enhanced surface-to-volume ratios, such as fluted or polylobed cylinders, can be employed to enhance mass transfer rates and, thus, catalytic activity.

In addition to the foregoing materials, the SSZ-25 zeolites can be composited with porous matrix materials and mixtures of matrix materials such as silica, alumina, titania, magnesia, silica:alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel.

The SSZ-25 zeolites can also be composited with other zeolites such as synthetic and natural faujasites (e.g., zeolites X and Y), erionites, and mordenites. They can also be composited with purely synthetic zeolites such as those of the ZSM series. The combination of zeolites can also be composited in a porous inorganic matrix.

SSZ-25 zeolites are useful in hydrocarbon conversion reactions. Hydrocarbon conversion reactions are chemical and catalytic processes in which carbon containing compounds are changed to different carbon containing compounds. Examples of hydrocarbon conversion reactions include catalytic cracking, hydrocracking, and olefin and aromatics formation reactions. The catalysts are useful in other petroleum refining and hydrocarbon conversion reactions such as isomerizing n-paraffins and naphthenes, polymerizing and oligomerizing olefinic or acetylenic compounds such as isobutylene and butene-1, reforming, alkylating, isomerizing polyalkyl substituted aromatics (e.g., ortho xylene), and disproportionating aromatics (e.g., toluene) to provide mixtures of benzene, xylenes and higher methylbenzenes. The SSZ-25 catalysts have high selectivity, and under hydrocarbon conversion conditions can provide a high percentage of desired products relative to total products.

SSZ-25 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, and, in general, can be any carbon containing fluid susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

Liquid Phase Alkylation of Aromatics

One particularly useful catalytic process that zeolite SSZ-25 catalyzes is the liquid phase alkylation of aromatics.

Examples of suitable aromatic hydrocarbon feedstocks which may be alkylated by the process of this invention include aromatic compounds such as benzene, toluene, ethylbenzene, xylenes, and cumene, naphthaline and biphenyl, or a mixture thereof. The preferred aromatic hydrocarbons are benzene, toluene, ethylbenzene and cumene, most preferably benzene.

Suitable olefins for the alkylation of the aromatic hydrocarbon are those containing 2 to 4 carbon atoms, such as ethylene, propylene, butene-1, trans-butene-2 and cis-butene-2, or mixtures thereof. Preferred olefins are ethylene and propylene. These olefins may be present in admixture with the corresponding $C_2$ to $C_4$ paraffins, but it is usually preferable to remove dienes, acetylenes, water, sulfur compounds or nitrogen compounds which may be present in the olefin feedstock stream, to prevent rapid catalyst deactivation. In some cases, however, it may be desirable to add, in a controlled fashion, small amounts of water or nitrogen compounds to optimize catalytic properties. For example, water may be added in cumene synthesis to control and reduce the formation of by-product n-propylbenzene. Water levels in the feed are generally maintained in the 10–150 ppm range.

Reaction products which may be obtained from the process of the invention include mono and polyalkylated aromatics where the alkyl group is derived from the alkylating agent, i.e., the olefin reaction products include ethylbenzene from the reaction of benzene with ethylene, cumene from the reaction of benzene with propylene, ethyltoluenes from the reaction of toluene with ethylene, cymenes from the reaction of toluene with propylene, sec-butylbenzene from the reaction of benzene with n-butenes, and di-isopropylbenzenes from the reaction of cumene with propylene. The production of ethylbenzene or cumene are especially preferred.

In a preferred embodiment, the present invention is a process for preparing short chain alkyl aromatic compounds which comprises contacting at least one alkylatable aromatic compound with at least one alkylating agent possessing an aliphatic group having from 2 to 4 carbon atoms under alkylation reaction conditions and in the presence of an alkylation catalyst to provide an alkylated aromatic product possessing at least one alkyl group derived from said alkylating agent, said catalyst comprising the calcined form of zeolite SSZ-25. When alkylation is conducted according to this invention, reaction conditions are as follows. The aromatic hydrocarbon feed should be present in stoichiometric excess. It is preferred that the molar ratio of aromatics to olefins be at least about two to one (2:1) to prevent rapid catalyst fouling. Higher ratios such as 3:1, 4:1 or 10:1 can also be used.

The reaction temperature may range from 100° F. to 600° F., preferably, 225° to 450° F. In the case of cumene production, a temperature range of 240° F. to 375° F. is useful. An average bed temperature of from 255° F. to 360° F. is preferred to reduce product impurities. It is desirable to operate at high enough temperatures to minimize catalyst fouling; however, it is also desirable to operate at low enough temperatures to reduce byproduct formation. For preparing chemicals, such as cumene and ethylene benzene, the effluent from the alkylation must, after single distillation, have a purity greater than 98%, preferably greater than 99%, more preferably, greater than 99.5%. It is preferred to operate the present process in an alkylator having at least two reactor stages, each stage containing alkylation catalyst. In this manner reactor temperature can be controlled through interbed injection and cooling. The alkylation catalyst in at least one of the stages is SSZ-25. Preferably, the alkylation catalyst in all the stages is SSZ-25.

The reaction pressure should be sufficient to maintain at least a partial liquid phase in order to retard catalyst fouling. This is typically 50 to 1000 psig depending on the feedstock and reaction temperature. Contact time may range from 10 seconds to 10 hours, but is usually from 5 minutes to an hour. The weight hourly space velocity (WHSV), in terms of pounds of aromatic hydrocarbon and olefin per pound of catalyst per hour, is generally within the range of about 0.5 to 50.

When the reactor is first brought on-stream, the catalyst activity may be too high to produce alkylated aromatics of desirable purity. For example, initially the amount of byproduct n-propyl benzene produced in cumene synthesis may be above commercial specifications. In this situation, the activity of the SSZ-25 catalyst can be mediated by adding small amounts of water. Alternatively, isopropyl alcohol, which can dehydrate to propylene and water, can be added. Various types of reactors can be used in the process of this invention. For example, the process can be carried out in batchwise fashion by adding the catalyst and aromatic feedstock to a stirred autoclave, heating to reaction temperature, and then slowly adding the olefinic or polyalkyl aromatic feedstock. A heat transfer fluid can be circulated through the jacket of the autoclave, or a condenser can be provided, to remove the heat of reaction and maintain a constant temperature. Large scale industrial processes may employ a fixed bed reactor operating in an upflow or downflow mode or a moving bed reactor operating with concurrent or countercurrent catalyst and hydrocarbon flows. These reactors may contain a single catalyst bed or multiple beds and may be equipped for the interstage addition of olefins and interstage cooling. Interstage olefin addition and more nearly isothermal operation enhance product quality and catalyst life. A moving bed reactor makes possible the continuous removal of spent catalyst for regeneration and replacement by fresh or regenerated catalysts. It is anticipated that catalytic distillation reactors would be especially effective for this type of reaction.

In a preferred embodiment of the present invention, the alkylation process is carried out with addition of olefin in at least two stages. Preferably, there will be two or more catalyst beds or reactors in series, wherein at least a portion of the olefin is added between the catalyst beds or reactors. Interstage cooling can be accomplished by the use of a cooling coil or heat exchanger. Alternatively, interstage cooling can be effected by staged addition of the aromatic feedstock, that is, by addition of the aromatic feedstock in at least two stages. In this instance, at least a portion of the aromatic feedstock is added between the catalyst beds or reactors, in similar fashion to the staged addition of olefin described above. The staged addition of aromatic feedstock provides additional cooling to compensate for the heat of reaction.

In one embodiment of this invention, the reaction stages are adiabatic, and all stages have about the same inlet and outlet temperatures. This is accomplished by adjusting the ratio of the aromatic hydrocarbon feed to the $C_2$ and $C_4$ olefin, which is fed between the catalyst beds. Higher ratios result in diluted olefins and provide more cooling from the aromatic hydrocarbon feed.

The alkylation reactor effluent contains the excess aromatic feed, monoalkylated product, polyalkylated products, and various impurities. The excess aromatic feed is recovered by distillation and recycled to the alkylation reaction. Usually a small bleed is taken from the recycle stream to eliminate unreactive impurities from the loop. The bottoms from the aromatic distillation are further distilled to separate monoalkylated product from polyalkylated products and other heavies. In most cases, the recovered monoalkylated product must be very pure. For example, current specifications call for 99.9% cumene purity with less than 500 ppm each of ethylbenzene and butylbenzene. Since only a small fraction of by-product ethylbenzene and n-propylbenzene can be economically removed by distillation, it is important to have a feedstock containing very little ethylene and a catalyst which makes very little of these impurities.

Additional monoalkylated product may be produced by transalkylation. The polyalkylated products may be recycled to the alkylation reactor to undergo transalkylation or they may be reacted with additional aromatic feed in a separate reactor. Usually, it is preferred to blend the bottoms from the distillation of monoalkylated product with a stoichiometric excess of the aromatic feed, and react the mixture in a separate reactor over a suitable transalkylation catalyst. The transalkylation catalyst is preferably a catalyst comprising zeolite Y or beta. The effluent from the transalkylation reactor is blended with alkylation reactor effluent and the combined stream distilled. A bleed may be taken from the polyalkylated product stream to remove unreactive heavies from the loop or the polyalkylated product stream may be distilled to remove heavies prior to transalkylation.

Reducing Benzene Content of Refinery Stream

The present invention provides a process for reducing the benzene content in a benzene-containing refinery stream such as a $C_4$-200° F. light reformate fraction. Typically, a full boiling range refinery stream can be fractionated by a distillation column wherein it is separated into a benzene-containing light fraction and a substantially benzene-free heavy fraction. Alternatively, a benzene-containing light fraction can be provided in any convenient manner. The benzene-containing light fraction contains less than 50 wt % benzene, preferably from about 1 to about 40 wt % benzene, more preferably from about 10 to about 30 wt % benzene.

The light fraction is alkylated in a nondistilling alkylation zone with light olefins, specifically $C_2$–$C_4$ olefins, more preferably with $C_2$–$C_3$ olefins, still more preferably with $C_3$ olefins. This is carried out in the presence of a specific alkylation catalyst under alkylation conditions which are selected to alkylate at least about 25% of the benzene initially present in the fraction, preferably at least about 35%, more preferably at least about 50% of such benzene, and still more preferably at least about 80% of such benzene.

The $C_2$–$C_4$ olefinic feedstreams which can be used in carrying out the invention can be pure or substantially pure feedstreams of the individual olefins or mixtures thereof. However, refinery streams containing such olefins along with other hydrocarbons can advantageously be used instead of essentially pure olefin containing streams, thus saving the costs of separating the olefins. Typical streams of this nature include, for example, FCC (fluid catalytic cracking) depropanizer overhead, which might typically contain 30 to 80 mole % propylene, about 5 mole % $C_4$ olefins and the balance $C_3$ and $C_4$ aliphatics and FCC off gas. Generally, the olefin containing stream can comprise an olefin-containing refinery stream having greater than 15 mole % of $C_2$–$C_4$ olefins along with other gaseous hydrocarbons.

Figure 1:
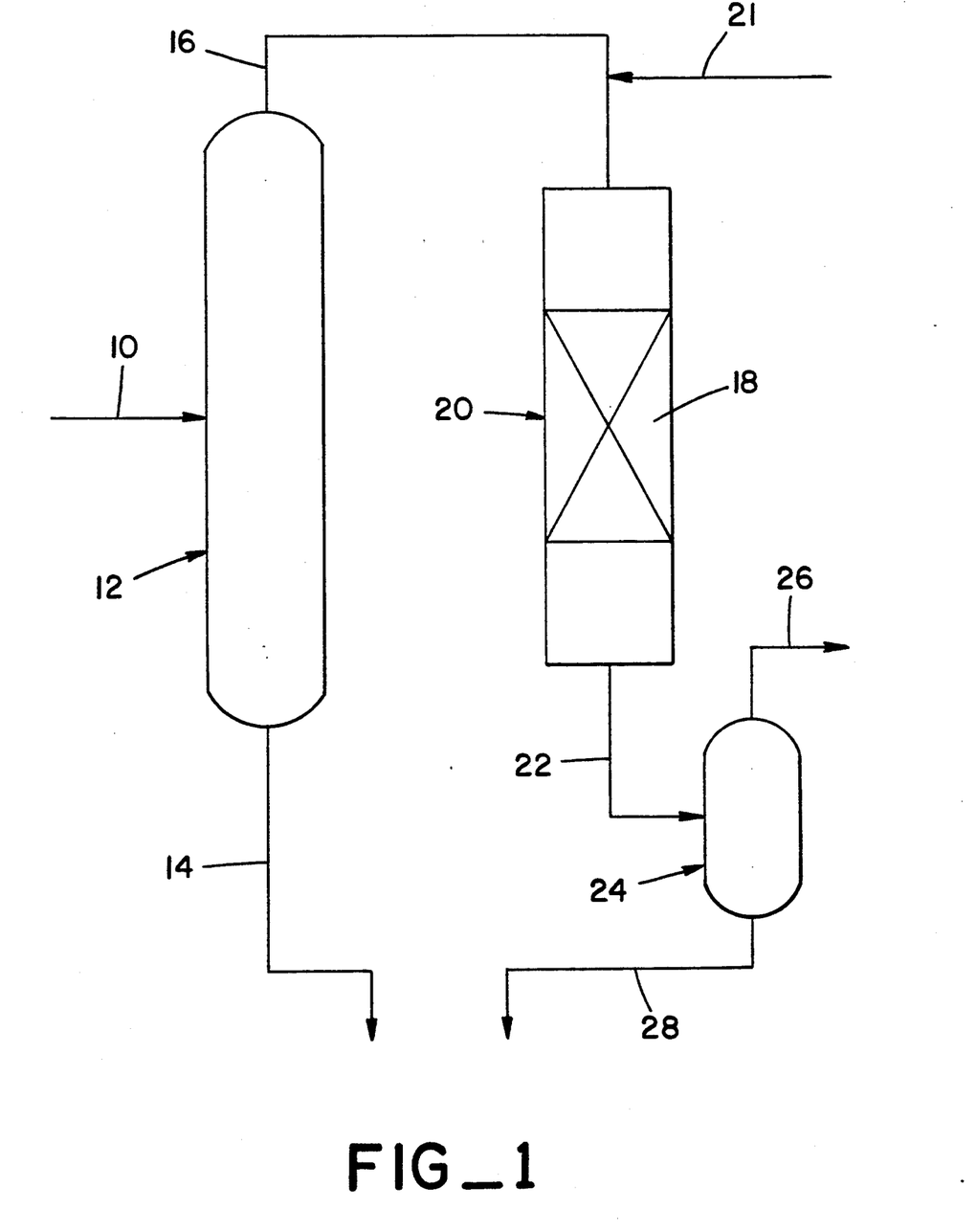
FIG. 1 is a schematic representation of an embodiment of a process in accordance with the present invention.

The term "nondistilling alkylation zone" as used herein is utilized to indicate a zone where the reaction products are not being continuously condensed within the reactor and removed as a heavy fraction and the condensible reactant, benzene, is not being continuously distilled away from and condensed and returning to the alkylation zone. This term is used to distinguish from a catalytic distillation alkylation zone wherein product (alkylated benzenes) and reactant (benzene) are continuously separated from one another by distillation. As is demonstrated in the examples, the relative efficiencies of different catalysts is unpredicatably different in these two different types of alkylation zone. FIG. 1 illustrates separation of a typical reformate into a bottoms fraction boiling above about 200° F. and a light benzene-containing fraction, followed by alkylation of the benzene-containing fraction in a nondistilling alkylation zone. The reformate, which might typically contain about 6 wt % benzene, is introduced via line 10 to distillation column 12 wherein it is separated into the bottoms fraction which exits via line 14 and the light benzene-containing fraction which exits via line 16. The light-benzene-containing fraction is introduced into a nondistilling alkylation zone 18 in a reactor vessel 20 along with a $C_2$–$C_4$ olefin containing stream entering via line 21. The reaction products exit the reactor vessel 20 via line 22 and are separated from one another in a separator 24 from which the C$_4$ components exit via line 26 and a substantially benzene-free stream exits via line 28. The substantially benzene-free stream serves as gasoline blending stock. If desired, it can be combined with the bottoms fraction exiting the distillation column 12 via line 14.

The alkylation conditions will generally include a temperature which falls within a range from about 200° F. to about 600° F., preferably from about 250° F. to about 550° F., more preferably from about 300° F. to about 450° F., a pressure which falls in a range above about 100 psig, preferably from about 100 psig to about 3500 psig, more preferably from about 100 psig to about 1000 psig, still more preferably from about 200 psig to about 800 psig, and a LHSV (liquid hourly space velocity) which is above about 0.1, and which preferably falls within a range from about 0.1 to about 30 and which more preferably falls within a range from about 0.1 to about 10. The molar ratio of total C$_2$-C$_4$ olefins to benzene will generally fall within a range from about 0.1 to about 10, preferably from about 0.5 to about 10, more preferably from about 0.5 to about 5.

Typical benzene alkylation conditions for reacting benzene in a light refinery stream are compared with typical alkylation conditions for cumene synthesis via benzene alkylation in Table 3.

TABLE 3

TYPICAL BENZENE ALKYLATION PROCESS CONDITIONS

| Parameter | Cumene Synthesis | Gasoline Benzene Reduction |
|---|---|---|
| Temp., °F. | 225–425 | 300–450 |
| Pres., psig | 400–600 | 200–600 |
| LHSV | 1–10 | 1–2 |
| Mole % benzene in aromatic feed | >98 | 10–30 |
| Mole % propylene in propylene feed | >70 | 5–100 |
| Per pass benzene conversion, % | ~10 | 25–90+ |
| Olefin:benzene molar ratio | 1:30 to 1:4 | 0.5:1 to 5:1 |

The time of reaction will vary depending upon the total amount of benzene present, the temperature chosen for the alkylation reaction, the pressure chosen for the alkylation reaction, the LHSV chosen for the alkylation reaction, and the total molar ratio of olefins to benzene. To minimize undesirable byproducts, it is preferred to have multiple injection points for the olefin into the alkylation zone, thereby reducing the chances for olefin polymerization, and to have multiple catalyst beds. Thus it is preferred to have two or more catalyst beds or reactors in series and to add a portion of the olefin between the catalyst beds or reactors.

Generally at least about 25%, preferably at least about 35% and more preferably at least about 50% of the benzene initially present in the light reformate fraction is alkylated in a single pass of the light reformate through the alkylation catalyst zone under the selected alkylation conditions thereby providing at least a 25% reduction in the benzene content of the resulting alkylated light hydrocarbon stream, preferably at least about 35% reduction, more preferably, at least about 50% reduction. Still more preferably at least about 80% of the benzene initially present is alkylated. Indeed, in accordance with the present invention it has been possible to obtain about 90% alkylation of the benzene initially present. The olefin to benzene ratio chosen for the alkylation reaction is largely determinative of the percent alkylation attained.

In those instances wherein a full boiling range reformate or other benzene containing refinery stream is fractionated to provide the benzene-containing light fraction which is alkylated in accordance with the invention, the cut off temperature in the distillation column which separates the light fraction from the heavy fraction can be set at a temperature between the boiling points of benzene and toluene, that is, between 176° and 231° F., for example, at 200° F. thereby preventing methyl, ethyl and propyl benzene derivatives from entering the alkylation zone since they are included in the heavy, 200° F.+ fraction. Refinery streams which can advantageously be treated in accordance with the process of the present invention include light reformate, light straight run gasoline, FCC light gasoline, coker light gasoline. As indicated previously, such streams are typically produced by fractionation which concentrates the benzene in the stream to be alkylated until it is present in an amount of up to a maximum of 50 wt %.

The invention will be better understood by reference to the following illustrative examples.

EXAMPLE 1

One Preparation of Zeolite SSZ-25

To prepare SSZ-25, the recipe in Example 3 of U.S. Pat. No. 4,826,667 was scaled up by a factor of 60. A small amount of SSZ-25 seed crystals were added to the reaction mix to facilitate crystallization. The crystallization was carried out in a half-gallon autoclave at 175° C. without stirring. After 10 days, a crystalline product was recovered by filtration. This product was washed with distilled water and dried in an oven at 100° C. An X-ray diffraction analysis confirmed that the product was SSZ-25 in its as synthesized form. Chemical analysis showed that this material had a SiO$_2$/Al$_2$O$_3$ ratio of 30.

A portion of the as synthesized material was calcined at 25°–600° C. and converted to its ammonium form by ion-exchange with ammonium nitrate as described in Examples 8 and 9 respectively of U.S. Pat. No. 4,826,667. The resulting product had the X-ray diffraction pattern of Table 2, supra.

EXAMPLE 2

Synthesis of SSZ-25 Using Reduced Amount of Adamantane Derivative

The cost of SSZ-25 zeolite may be reduced by partially substituting a less costly amine for templates A or B used in the original preparations described in Examples 1 to 7 of U.S. Pat. No. 4,826,667, which is incorporated herein by reference.

For example, 18 grams of a 0.55 M solution of Template B (N,N,N-trimethyl-2-adamantammonium hydroxide) were mixed with 7.67 grams of piperidine, 0.17 grams of SSZ-25 seeds, 89.5 grams of 1.0 M potassium hydroxide, 2.50 grams of Reheis F-hydrated alumina, and 250 mL of deionized water. After thorough mixing, 27 grams of fumed silica (Cab-O-Sil, Cabot Corporation) was blended into the mix as a silica source. The final mixture was heated in a Teflon-lined, 1-liter Parr reactor at 170° C. at 50 RPM for seven days.

The as synthesized washed and oven-dried crystals were calcined at 463° C. for two hours and ammonium exchanged, using the same mass of NH$_4$NO$_3$ as zeolite and mixing in water at a ratio of 50:1 water:zeolite. The exchange solution was heated at 100° C. for two hours and filtered; this was repeated four times. Finally, the zeolite was washed several times with water and dried. The calcined material was identified by its X-ray powder diffraction pattern (Table 2) as zeolite SSZ-25.

EXAMPLE 3

Ethylbenzene Synthesis over Zeolite SSZ-25

The zeolite powder of Example 1 in its ammonium form was pressed into tablets which were then crushed and sieved to obtained 10-20 mesh granules. The catalyst granules were calcined in a furnace at 1000° F. for 4 hours to convert the zeolite to its hydrogen form.

The resulting SSZ-25 catalyst was tested for ethylbenzene synthesis activity as follows. The reaction was carried out in an upflow liquid-phase mode. The bottom portion of a ⅜-inch diameter tubular microreactor was filled with quartz granules to act as a preheat zone. Two grams of catalyst were charged on top of the quartz bed. Dry nitrogen was flowed over the catalyst while the reactor was heated to reaction temperature by a three-zone electric furnace. The temperature was measured by a sheathed thermocouple located just above the catalyst bed. The reactor was then pressurized to 450 psig with nitrogen. After reaching 450 psig, the nitrogen flow was switched from the reactor inlet to a point downstream of the reactor outlet and liquid benzene was fed to the reactor inlet at a rate of 12 mL/hr. The diluent nitrogen vaporized the reaction products and the combined stream flowed out through the pressure letdown valve. The effluent was analyzed every two hours by an on-stream gas chromatograph. After the GC analysis confirmed that the reactor was filled with liquid benzene, 0.544 grams/hour of ethylene gas was added to the benzene feed stream. These flow rates correspond to a WHSV (grams of benzene+grams of ethylene per gram of catalyst) of 5.6 and a benzene to ethylene molar ratio of 7.0.

Table 4 shows ethylene conversions and product compositions obtained during the ethylbenzene synthesis. The product compositions are on are a benzene-free weight basis.

TABLE 4

| Hours Onstream | 24-48 | 54-72 | 78-96 | 150-168 |
|---|---|---|---|---|
| Temperature, °F. | 400 | 325 | 375 | 350 |
| Ethylene Conversion, % | 100 | 83 | 98 | 88 |
| Products, Wt % | | | | |
| Ethylbenzene | 92.4 | 93.6 | 92.5 | 93.1 |
| 1,3-Diethylbenzene | 1.9 | 1.3 | 1.7 | 1.5 |
| 1,2-Diethylbenzene | 3.3 | 3.0 | 3.6 | 3.3 |
| 1,4-Diethylbenzene | 1.4 | 1.2 | 1.4 | 1.3 |
| 1,3,5-Triethylbenzene | 0.2 | 0.1 | 0.2 | 0.1 |
| Other | 0.8 | 0.7 | 0.7 | 0.7 |

EXAMPLE 4

Cumene Synthesis over Zeolite SSZ-25

This example was carried out in the same manner as Example 3 except that propylene was fed instead of ethylene and the reaction pressure was 600 psig. The propylene feed rate was 1.5 mL of liquid per hour. WHSV was 5.7 with a benzene to propylene molar ratio of 7.8. The cumene synthesis results are shown in Table 5.

TABLE 5

| Hours Onstream | 50-72 | 98-120 | 146-170 |
|---|---|---|---|
| Temperature, °F. | 325 | 325 | 325 |
| Propylene Conversion, % | 100 | 100 | 100 |
| Products, Wt % | | | |
| Ethylbenzene | 0.02 | 0.02 | 0.01 |
| Cumene | 90.1 | 90.4 | 90.5 |
| n-Propylbenzene | 0.04 | 0.04 | 0.04 |
| 1,3-Diisopropylbenzene | 2.6 | 2.5 | 2.4 |
| 1,4-Diisopropylbenzene | 5.1 | 5.0 | 4.9 |
| Other | 2.2 | 2.2 | 2.0 |

EXAMPLE 5

Cumene Synthesis over Alumina Bound SSZ-25

A 347 gram aliquot of SSZ-25 was mixed with 116.5 grams of CATAPAL TM alumina powder. The mixed powders were then placed in a Baker-Perkins mixer and a total of 169.5 grams of water was added as a spray while mixing. A dilute mixture of nitric acid comprised of 52.5 grams of water plus 4.1 grams of concentrated nitric acid was sprayed onto the material while mixing was continued. Mixing was continued until the material was of extrudable consistency. Water was added as necessary to achieve proper consistency. The material was then placed in a Fuji extruder with a 1/16 inch dye and extruded. The extrudate was dried at 248° F. overnight and was then calcined at 1000° F. overnight resulting in the finished alumina bound SSZ-25 catalyst.

The extrudates were broken into ¼-inch long pieces for testing. The procedure was the same as in Example 4 above except that 2.5 grams of catalyst were charged to the microreactor. The results of cumene synthesis over the alumina bound catalyst are shown in Table 6.

TABLE 6

| Hours Onstream | 8-18 | 20-42 | 44-66 |
|---|---|---|---|
| Temperature, °F. | 325 | 325 | 325 |
| Propylene Conversion, % | 100 | 100 | 100 |
| Products, Wt % | | | |
| Ethylbenzene | 0.00 | 0.00 | 0.00 |
| Cumene | 91.1 | 91.5 | 91.7 |
| n-Propylbenzene | 0.04 | 0.04 | 0.04 |
| 1,3-Diisopropylbenzene | 2.4 | 2.1 | 2.2 |
| 1,4-Diisopropylbenzene | 4.4 | 4.3 | 4.5 |
| Other | 2.0 | 2.1 | 1.6 |

EXAMPLE 6

Cumene Synthesis at Low Benzene/Propylene Ratio

An alumina bound SSZ-25 catalyst prepared in the manner described in Example 1 was tested as described in Example 5 except that the benzene to propylene feed molar ratio was reduced from 7.8 to 3.4 by reducing the benzene feed rate. The catalyst exhibited excellent stability even though operating at a lower aromatic to olefin ratio than is normally used with zeolite catalysts. The results are shown in Table 7.

TABLE 7

| CUMENE VIA INTERBED INJECTION OF BENZENE AND PROPYLENE | | | |
|---|---|---|---|
| Hours Onstream | 20-42 | 236-258 | 498-520 |
| Temperature, °F. | 325 | 325 | 325 |
| Propylene Conversion, % | 100 | 100 | 100 |
| Products, Wt % | | | |
| Ethylbenzene | 0.00 | 0.00 | 0.00 |
| Cumene | 81.9 | 82.1 | 82.1 |
| n-Propylbenzene | 0.04 | 0.03 | 0.03 |
| 1,3-Diisopropylbenzene | 6.0 | 5.2 | 5.0 |

TABLE 7-continued
CUMENE VIA INTERBED INJECTION OF BENZENE AND PROPYLENE

| | | | |
|---|---|---|---|
| 1,4-Diisopropylbenzene | 9.6 | 9.9 | 9.8 |
| Other | 2.3 | 3.0 | 3.2 |

EXAMPLE 7

Cumene Synthesis with Interbed Injection of Benzene and Propylene

This example illustrates the use of interstage injection of benzene and propylene to increase run length and product purity. The reaction is carried out in an adiabatic reactor containing three catalyst beds. The reactor operates in a liquid-phase, upflow mode. Best results are obtained when the reactor exotherm is equally distributed across the three catalyst beds and the inlet temperatures are the same for the three beds. For maximum run length, the plant is operated at as high a catalyst bed temperature as possible without exceeding maximum specifications for n-propylbenzene in final cumene product. The bed inlet temperature is typically between 240° F. and 320° F. and the outlet temperature is typically between 285° F. and 365° F.

A liquid mixture of benzene and propylene in a 23/1 volumetric ratio is heated to the desired reactor inlet temperature and fed to the bottom of the reactor. The alkylation reaction is exothermic resulting in about a 45° F. temperature rise across the first catalyst bed. Cold benzene and propylene is a 3.5/1 volumetric ratio are injected into and mixed with the effluent from the first catalyst bed so that the combined stream enters the second catalyst bed temperature at about the original reactor inlet temperature. There is about 45° F. exotherm across the second catalyst bed and once again the effluent is cooled by the injection of benzene and propylene in a 3.5/1 ration. The inlet temperature for the third catalyst bed is about the same as for the first and second catalyst beds and the exotherm across bed #3 is against about 45° F. The amount of propylene added at each stage increases in a ratio of 1.0/1.2/1.4 so that the overall ratio of benzene to propylene fed is about 9.0 vol/vol.

All of the propylene is converted. The reactor effluent contains about 91–94% cumene on a benzene-free weight basis. The byproduct diisopropylbenzene fraction is rich in para-isomer.

EXAMPLE 8

Cumene Synthesis over Zeolite SSZ-25 from Example 2

The ammonium exchanged SSZ-25 from Example 2 was calcined at 1000° F. to convert it to its hydrogen form. The H-SSZ-25 was tested as a catalyst for cumene synthesis using the same procedure and equipment as Example 4. The results are shown in Table 8.

TABLE 8

| Hours Onstream | 49–65 | 307–329 | 620–642 |
|---|---|---|---|
| Temperature, °F. | 325 | 325 | 325 |
| Propylene Conversion, % | 100 | 100 | 100 |
| Product Wt % | | | |
| Ethylbenzene | 0.02 | 0.00 | 0.00 |
| Cumene | 91.7 | 92.2 | 93.2 |
| n-Propylbenzene | 0.06 | 0.05 | 0.05 |
| 1,3-Diisopropylbenzene | 2.7 | 2.0 | 1.8 |
| 1,4-Diisopropylbenzene | 4.4 | 4.3 | 4.0 |
| Other | 1.2 | 1.4 | 1.0 |

EXAMPLE 9

Preparation of Light Reformate Feed

A light reformate, benzene containing stream was prepared by distilling a typical high octane full boiling range reformate feed obtained from a commercial reformer. The reformate feed and the light reformate had the following properties:

TABLE 9

| | Full Range Reformate | Light Reformate |
|---|---|---|
| Component. wt % | | |
| Benzene | 5.3 | 20.0 |
| Toluene | 19.7 | 3.4 |
| $C_8$ aromatics | 23.9 | 0.0 |
| TBP Distillation, °F. | | |
| Volume % | | |
| 5 | 154 | 110 |
| 10 | 179 | 119 |
| 30 | 230 | 141 |
| 50 | 263 | 154 |
| 70 | 293 | 166 |
| 90 | 334 | 186 |
| 95 | 352 | 205 |
| RON clear | 101 | 78 |
| MON clear | 91 | 75 |
| Gravity, API | 42 | 70 |

Where RON and MON are research and motor octane numbers, respectively.

EXAMPLE 10

Preparation of Propylene Feed

Polymer grade propylene of 99% purity was obtained from a gas supplier and used without any further purification.

EXAMPLE 11

Preparation of a Simulated FCC Off Gas

A simulated FCC off gas was prepared by mixing various gases to arrive at the following composition:

TABLE 10

| Composition | Volume % |
|---|---|
| Hydrogen | 80 |
| Ethylene | 15 |
| Propylene | 5 |

It is recognized that typically FCC off gas contains methane, ethane, and propane and only ~30% hydrogen. The mixture shown above was chosen for experimental ease only. It does contain the typical amount of $C_2$ and $C_3$ olefins that are found in typical FCC Off Gas.

EXAMPLE 12

Preparation of a Ethylene Feedstock

Polymer grade ethylene (99.8% purity) was obtained from a gas supplier. In some of the following examples it was used without dilution and in other examples it was diluted with hydrogen.

EXAMPLE 13

Alkylation of Light Reformate with Ethylene

A five gram aliquot of SSZ-25 extrudate prepared as set forth in Example 5 was ground to 24–80 mesh and charged to a stainless steel nondistilling reactor. Pure ethylene was introduced at the reactor inlet (top) at about ~500 cc/min and the pressure was increased to 400 psig. The ethylene rate was then reduced to 17 cc/min. Next a feed similar to that in Example 1 but with a benzene content of 22.7 wt % was introduced at the reactor inlet at a rate of 5 cc/hr. Finally, the catalyst was heated to 600° F.

Analyses of the reactor effluent showed the following:

| Benzene Conversion | 70 mole % |
|---|---|
| Ethylene conversion | 78 mole % |
| $C_{5}+$ Liquid Yield | 120 LV % |
| RON (calculated) | 86 |

The data shows that high benzene conversions are obtained with SSZ-25 catalyst and ethylene. Increases in liquid yield and product octane also resulted.

EXAMPLE 14

Alkylation of Light Reformate with Propylene

A fifty cc aliquot of SSZ-25 whole extrudate prepared as set forth in Example 5 was loaded into a 0.96 ID stainless steel reactor and operated in a nondistilling, fixed bed configuration. The catalyst was heated in flowing nitrogen at atmospheric pressure to about 350° F. and held overnight. Then nitrogen was stopped and the reactor pressure was increased to 400 psig using hydrogen. With the catalyst bed at about 350° F. light reformate similar to Example 9 was introduced to the reactor inlet (top) at a rate of 75 cc/hr. This feed contained 26 wt % benzene. Hydrogen was also added at the reactor inlet at a rate of 50 cc/hr to aid in controlling pressure. Approximately 1 hour after light reformate introduction, propylene feed from Example 10 was introduced at the reactor inlet at a rate sufficient to give a propylene to benzene mole ratio of 1:1. These conditions were maintained for 300 hours of operation. Then the propylene to benzene ratio was increased to 1.5:1 by adjusting the propylene feed rate.

Analyses of the reactor effluent liquid product are summarized in Table 11.

TABLE 11

| Propylene/Benzene | 1.0 | 1.5 |
|---|---|---|
| Benzene Conversion, % | 62 | 78 |
| Propylene Conversion, % | 97 | 97 |
| Composition, wt % | | |
| $C_4$'s | 1.1 | 0.7 |
| $C_5$'s | 10.8 | 10.1 |
| $C_6$'s (P + O + N) | 30.8 | 30.3 |
| Benzene | 8.0 | 5.4 |
| $C_7$'s (P + O + N) | 14.8 | 14.7 |
| Toluene | 2.1 | 1.3 |
| $C_8$'s | 0.8 | 0.5 |
| $C_8$ Aromatic | 0.2 | 0.1 |
| $C_9$'s | 0.2 | 0.1 |
| Cumene | 16.1 | 17.7 |
| $C_{10}$'s | 0.4 | 0.2 |
| Cymenes | 3.4 | 3.9 |
| $C_{11}$'s | 1.9 | 1.7 |
| Diisopropylbenzene | 5.4 | 9.1 |
| $C_{12}+$ | 2.8 | 4.1 |
| $C_{5}+$ LV % of Feed | 112 | 117 |
| RON | 84.0 | 86.4 |
| MON | 80.9 | 84.3 |

The data shows that SSZ-25 is very effective at reducing the benzene content of light reformate by alkylation with propylene. Benzene conversion is >60% and increases with increasing propylene to benzene ratio. There is also a significant increase in $C_{5}+$ liquid yield and RON relative to the light reformate feed.

EXAMPLE 15

Alkylation of Light Reformate with Propylene

The same catalyst as was used in Example 14 was contacted with a light reformate containing 23 wt % benzene and propylene. The propylene rate was set to give a propylene to benzene mole ratio of 2:1. Other conditions were the same as in Example 14. The results summarized in Table 12 show that benzene conversions of up to 90% are possible with SSZ-25 catalyst.

TABLE 12

| Propylene/Benzene | 2.0 |
|---|---|
| Benzene Conversion | 90.0 |
| Propylene Conversion | 90.0 |
| Composition, wt % | |
| $C_4$'s | 1.3 |
| $C_5$'s | 11.6 |
| $C_6$'s | 29.3 |
| Benzene | 2.0 |
| $C_7$'s | 15.7 |
| Toluene | 0.5 |
| $C_8$'s | 0.4 |
| $C_8$ Aromatic | 0.1 |
| $C_9$'s | 0.1 |
| Cumene | 12.3 |
| $C_{10}$'s | 0.3 |
| Cymenes | 2.0 |
| $C_{11}$'s | 0.4 |
| Diisopropylbenzene | 14.7 |
| $C_{12}+$ | 9.3 |
| $C_{5}+$ LV % of Feed | 113 |
| RON | 88.1 |
| MON | 85.0 |

EXAMPLE 16

Preparation of Beta Zeolite Catalyst

A beta zeolite catalyst was prepared and tested for comparison purposes. A 524.06-gram portion of Ludox AS-30 silica sol was added dropwise to 20.05 gms of sodium aluminate, $Na_2Al_2O_43H_2O$ and 652.22 gms of 20% tetraethylammonium hydroxide solution. The mixture was stirred for two days without heat, then charged to a one-gallon autoclave. After six days in the autoclave at 150° C. and without stirring, a large amount of crystalline material was formed. This material was filtered, washed, and oven-dried overnight at 100° C. to yield 141 gms of crystalline powder. The oven-dried material was calcined for 10 hours at 1000° F. Both the air-dried and calcined materials were identified by X-ray diffraction as beta zeolite.

Two more batches of beta zeolite were prepared identically to the first batch except that the amounts of the starting materials used were multiplied by 0.61 and 1.22 to yield 89.7 and 195.5 gms of oven-dried zeolite, respectively. In both cases, X-ray diffraction patterns confirmed that the oven-dried and calcined products were beta zeolite.

The combined calcined material was analyzed by ICP spectroscopy. The Si/Al atomic ratio was 13/1 and the sodium content was 0.3 weight percent. The surface area of the calcined zeolite measured by the nitrogen adsorption was 640 m²/g.

A 355 gram portion of calcined beta zeolite was divided into three equal portions which were each ammonium exchanged four times. The exchanges were carried out by soaking the zeolite in approximately two liters of 0.7 N ammonium nitrate solution overnight at 212° F. After each of the first three exchanges, the supernatent liquid was decanted off and fresh ammonium nitrate solution added. After the final exchange, the product was filtered, washed with distilled water, and oven-dried.

This ammonium-exchanged beta zeolite was calcined for five hours at 1000° F. to convert the zeolite to its hydrogen form. A 320-gram portion of the calcined zeolite was dry-mixed with 112.7 gms of Catapal alumina (71% $Al_2O_3$). Distilled water and dilute nitric acid were added to peptize the alumina and bring the mixture to a consistency suitable for extrusion. A hydraulic press was used to extrude the mixture through a 1/16-inch die. The extrudates were collected in a large evaporating dish, oven-dried, then calcined at 400°-1000° F.

COMPARATIVE EXAMPLE 17

Beta Zeolite in a Fixed Bed

Figure 2:
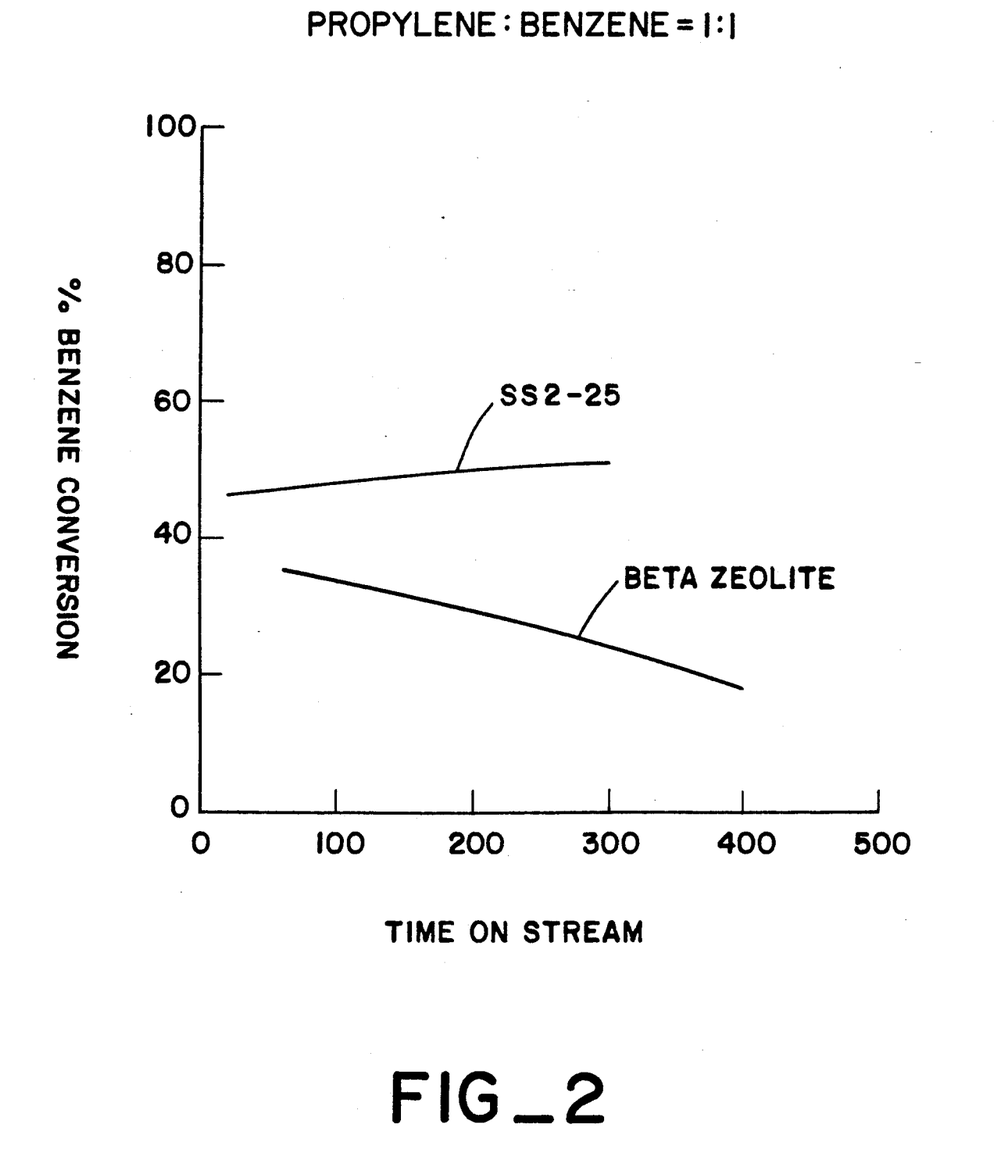
FIG. 2 is a graphical comparison of benzene alkylation using a zeolite SSZ-25 catalyst and beta zeolite in nondistilling fixed bed reactors.

Beta zeolite, synthesized as set forth in Example 16, was tested in a manner similar to that described in Example 15 for SSZ-25. A plot of the benzene conversion as a function of time on stream is shown in FIG. 2. It is evident that, although SSZ-25 and beta are both zeolites, SSZ-25 is clearly superior in terms of both benzene conversion and stability when alkylating benzene in a reformate stream. This further demonstrates the unpredictability of the catalysts for benzene alkylation.

EXAMPLE 18

Alkylation of Light Reformate with Simulated FCC Off Gas

The same catalyst as was used in Example 14 was contacted with light reformate containing 23.2 wt % benzene and a simulated FCC Off Gas. The composition of the Off Gas is given in Example 11. The rate of the Off Gas was adjusted to give a total olefin to benzene mole ratio of 1.5:1. The catalyst temperature was 500° F. Other conditions were the same as in Example 14. The following Table 13 summarizes the results.

TABLE 13

| | |
|---|---|
| $H_2$/Benzene | 6.4 |
| Ethylene/Benzene | 1.2 |
| Propylene/Benzene | 0.3 |
| Benzene Conversion | 40.0 |
| Ethylene Conversion | 10.0 |
| Propylene Conversion | 91.0 |
| Composition, wt % | |
| $C_4$'s | 0.2 |
| $C_5$'s | 9.4 |
| $C_6$'s | 35.6 |
| Benzene | 14.3 |
| $C_7$'s | 19.7 |
| Toluene | 2.7 |
| $C_8$'s | 0.4 |
| $C_8$ Aromatic | 2.5 |
| $C_9$'s | 0.2 |
| Cumene | 10.3 |
| $C_{10}$'s | 0.3 |
| Cymenes | 1.5 |
| $C_{11}$'s | 0.8 |
| DIPB | 1.4 |
| $C_{12}+$ | 0.2 |
| $C_5+$ LV % of Feed | 111 |
| RON | 80.3 |

This example shows that SSZ-25 is effective at reducing the benzene content of the light reformate using a dilute $C_2$ and $C_3$ olefin feed stream. There is also an increase in liquid volume and RON.

EXAMPLE 19

Preparation of a Simulated FCC Off Gas

A simulated FCC off gas was prepared by mixing various gases to arrive at the following composition:

| Composition | Volume % |
|---|---|
| Hydrogen | 30 |
| Methane | 30 |
| Ethane | 15 |
| Ethylene | 15 |
| Propane | 5 |
| Propylene | 5 |

EXAMPLE 20

Comparative Example: Benzene Alkylation in a Catalytic Distillation Reactor Versus Benzene Alkylation in a Fixed Bed This comparative example demonstrates that the chemistry of benzene alkylation is sensitive to the type of reactor used as well as to the type of alkylation catalyst, thus illustrating the unpredictable nature of the alkylation catalysts.

A catalytic distillation reactor was prepared by packing two zones of catalyst and three zones of distillation packings into a 1¼ inch o.d. by 4-foot long steel tube. Each zone of catalyst contained about 100 cc of catalyst and the two zones were separated with a 4-inch long zone of Penn State packings. Overhead reflux and bottoms reboiling loops were provided. The pressure of the pilot plant was maintained with back pressure regulation and the temperatures of different areas were controlled with individual heaters. Two concurrent flow regime experiments were conducted, one used beta zeolite catalyst of Example 16 and the other used SSZ-25 catalyst of Example 5. Both experiments used a simulated FCC off gas as set forth in Example 19 and a light reformate feed similar to that of Example 9. The feed contained 22.5 % benzene. The reactor pressure was maintained at 200 psig and the reactor temperature profile was maintained such that it had a mid temperature of 430° F. The gas rate was maintained at about 1.3 moles/hr for both experiments. The feed rate was 140 grams/hr and 112 grams/hr for beta zeolite and SSZ-25, respectively. The overhead reflux ratio was maintained at 3. The following results were obtained.

| | Beta Zeolite | SSZ-25 |
|---|---|---|
| Benzene Conversion, % | 32 | 31 |

Comparing the catalytic distillation reactor results in this example to the fixed bed reactor results in Example 17 (FIG. 2) shows that although SSZ-25 and beta zeolite are about equally effective in a catalytic distillation reactor, there is a significant difference in the performance of the two catalysts when the reaction is carried out in a fixed bed reactor. Thus, SSZ-25 is effective at alkylating benzene in both fixed bed and catalytic distillation reactors configurations. Beta zeolite on the other hand is not. This further demonstrates the unique behavior of SSZ-25 for alkylation of a benzene-containing feedstocks having less than 50 wt % benzene.

INDUSTRIAL APPLICABILITY

The present invention provides a process for reducing the benzene content of a refinery stream to produce a gasoline blend stock having a low benzene content.

While the invention has been described in connection with specific embodiments thereof, it will be understood that it is capable of further modifications, and this application is intended to cover any variations, uses, or adaptations of the invention following, in general, the principles of the invention and including such departures from the present art to which the invention hereinbefore set forth, and as fall within the scope of the invention and the limits of the appended claims.

What is claimed is:

1. A hydrocarbon conversion process comprising using calcined SSZ-25 zeolite under hydrocarbon conversion conditions in the reaction of alkylating wherein said zeolite has the X-ray diffraction lines of Table 2.

2. The process according to claim 1 wherein the process comprises contacting a stoichiometric excess of an aromatic hydrocarbon with a $C_2$ to $C_4$ olefin under at least partial liquid phase conditions and in the presence of a catalyst comprising zeolite SSZ-25, wherein the molar ratio of aromatic hydrocarbon to olefin is at least about 2:1.

3. The process according to claim 2, wherein the molar ratio of aromatic hydrocarbon to olefin is at least about 4:1.

4. The process according to claim 2, wherein the aromatic hydrocarbon is a member selected from the group consisting of benzene, toluene, ethylbenzene, cumene, and xylenes, naphthalene, bipheyl or mixtures thereof.

5. The process according to claim 3, wherein the aromatic hydrocarbon is benzene.

6. The process according to claim 2, wherein the olefin is a member selected from the group consisting of ethylene, propylene, butene-1, trans-butene-2 and cis-butene-2, or mixtures thereof.

7. The process according to claim 5, wherein the olefin is propylene.

8. The process according to claim 5, wherein the olefin is ethylene.

9. The process according to claim 2, wherein the alkylation reaction is carried out at a temperature in the range of about 225° F. to 450° F. and a pressure in the range of about 50 psig to 1000 psig.

10. The process according to claim 7 wherein the temperature is in the range of 240° to 375° F.

11. The process according to claim 2, wherein the alkylation reaction is carried out at a weight hourly space velocity of about 0.5 to 50.

12. The process according to claim 2, wherein a major portion of the cation sites in the zeolite SSZ-25 are occupied by hydrogen ions.

13. The process according to claim 12, wherein the zeolite SSZ-25 has a silica to alumina mole ratio greater than 10:1 and less than 200:1.

14. The process according to claim 13, wherein the zeolite SSZ-25 has a silica to alumina mole ratio greater than 10:1 and less than 50:1.

15. The process according to claim 14, wherein the zeolite SSZ-25 has a silica to alumina mole ratio greater than 15:1 and less than about 40:1.

16. The process according to claim 2, wherein the zeolite SSZ-25 is combined with an inorganic oxide binder in an amount ranging from about 1 to 99 weight percent of zeolite SSZ-25.

17. The process according to claim 15, wherein the inorganic oxide binder is alumina.

18. The process according to claim 2, wherein the aromatic hydrocarbon is benzene and the olefin is propylene.

19. The process according to claim 2, wherein the aromatic hydrocarbon is benzene and the olefin is ethylene.

20. The process according to claim 2, wherein the aromatic hydrocarbon is benzene and the olefin is propylene.

21. The process according to claim 2, wherein the olefin is added in at least two stages.

22. The process according to claim 21, wherein there are two or more catalyst beds or reactors in series and at least a portion of the olefin is added between the catalyst beds or reactors.

23. A process for alkylating an aromatic hydrocarbon by reacting an aromatic hydrocarbon and a $C_2$ and $C_4$ olefin in the presence of a SSZ-25 alkylation catalyst, said process comprising introducing a mixture of aromatic hydrocarbon and $C_2$ to $C_4$ olefin into the first stage of an alkylator having at least two reactor stages, each stage containing alkylation catalyst, and mixing the effluent from each reactor stage with a fresh mixture of aromatic hydrocarbon and $C_2$ and $C_4$ olefin prior to introduction of said effluent to the next reactor stage, wherein the alkylation catalyst in one of the reactor stages is SSZ-25.

24. The process of claim 23 wherein the temperature conditions of all reactor stages are essentially the same.

25. The process of claim 23 wherein each reactor stage is adiabatic and wherein the mixture of aromatic hydrocarbon and $C_2$ and $C_4$ olefin is introduced at the inlet of each reactor stage.

26. The process of claim 23 wherein the ratio of aromatic hydrocarbon to $C_2$ to $C_4$ olefin in the mixtures introduced into each reactor stage is such that the temperature of the reaction mixture at the outlet of each reactor stage is essentially the same.

27. The process of claim 23 wherein said ratio of aromatic hydrocarbon to $C_2$ to $C_4$ olefin is sufficiently high at each reactor stage to minimize fouling while still meeting product specifications.

28. The process of claim 23 wherein the mixture of aromatic hydrocarbon and $C_2$ and $C_4$ olefin introduced into the first stage contains the majority, but not all, of the aromatic hydrocarbon used in the process.

29. The process of claim 23 wherein the alkylation catalyst in all of the reactor stages is zeolite SSZ-25.

30. A process for preparing monoalkylated aromatic hydrocarbons which comprises:
 (a) alkylating an aromatic hydrocarbon by reacting an aromatic hydrocarbon and a $C_2$ to $C_4$ olefin in the presence of an alkylation catalyst by introducing a mixture of aromatic hydrocarbon having at least two reactor stages, each stage containing alkylation catalyst, and mixing the effluent from each reactor stage with a fresh mixture of aromatic hydrocarbon and $C_2$ and $C_4$ olefin prior to introduction of said effluent to the next reactor stage;
 (b) separating the product from step (a) into fractions comprising:
  (1) an aromatic hydrocarbon fraction,
  (2) monoalkyl aromatic hydrocarbon fraction, and
  (3) a polyalkyl aromatic hydrocarbon fraction; and (c) contacting the polyalkyl aromatic hydrocarbon fraction with additional aromatic hydrocarbon feed in a transalkylation zone under at least partial liquid phase conditions and in the presence of a transalkylation catalyst, wherein the alkylation catalyst in one of the reactor stages of step (a) is SSZ-25.

31. The process of claim 30 wherein the alkylation catalyst in all of the reactor stages is SSZ-25.

32. A process for preparing monoalkylated aromatic hydrocarbons which comprises:
(a) contacting a stoichiometric excess of an aromatic hydrocarbon feed with a $C_2$ to $C_4$ olefin in an alkylation zone under at least partial liquid phase conditions and in the presence of a catalyst comprising zeolite SSZ-25;
(b) separating the product from step (a) into fractions comprising (1) an aromatic hydrocarbon fraction, (2) a monoalkyl aromatic hydrocarbon fraction and (3) a polyalkyl aromatic hydrocarbon fraction; and
(c) contacting the polyalkyl aromatic hydrocarbon fraction with additional aromatic hydrocarbon feed in a transalkylation zone under at least partial liquid phase conditions and in the presence of a transalkylation catalyst.

33. The process of claim 32, where the transalkylation catalyst comprises a Y zeolite or a beta zeolite.

34. The process as set forth in claim 1 wherein the process comprises treating a benzene-containing light hydrocarbon stream having less than 50 weight percent benzene to form a gasoline blending stock having a reduced benzene content, comprising: contacting the benzene-containing light hydrocarbon stream with a $C_2$-$C_4$ olefin containing stream in an alkylation zone containing an SSZ-25 catalyst under alkylation conditions to produce an alkylated light hydrocarbon stream having a benzene content reduced by at least 25% as compared to that in the benzene-containing light hydrocarbon; and utilizing the alkylated light hydrocarbon stream as gasoline blend stock.

35. A process as set forth in claim 34, wherein said alkylation conditions include a temperature which falls within a range from about 200° F. to about 600° F., a pressure which falls within a range from about 100 psig to about 1000 psig, and a LHSV which falls within a range from about 0.1 to about 10, and wherein the molar ratio of total olefins to benzene falls within a range of about 0.5 to about 10.

36. A process as set forth in claim 35, further including obtaining said benzene-containing light hydrocarbon stream by: introducing a full boiling range benzene containing refinery stream into a distillation column to produce a bottoms fraction which is substantially benzene-free and said benzene-containing light hydrocarbon stream; and transferring said benzene-containing light hydrocarbon stream to said alkylation zone.

37. A process as set forth in claim 36, wherein the olefin stream comprises an olefin-containing refinery stream having greater than 15 mole % of $C_2$-$C_4$ olefins along with other gaseous hydrocarbons.

38. A process as set forth in claim 37, wherein the benzene content in the alkylated light hydrocarbon stream is reduced by at least 50%.

39. A process as set forth in claim 38, wherein the benzene content in the alkylated light hydrocarbon stream is reduced by at least 80%.

40. A process as set forth in claim 39, wherein the benzene-containing light hydrocarbon stream has from about 1 wt % to about 40 wt % benzene.

41. A process as set forth in claim 34, wherein the olefin stream comprises an olefin-containing refinery stream having greater than 15 mole % of $C_2$-$C_4$ olefins along with other gaseous hydrocarbons.

42. A process as set forth in claim 41, wherein said alkylation conditions include a temperature which falls within a range from about 250° F. to about 555° F., a pressure which falls within a rang from about 100 psig to about 1000 psig, and a LHSV which falls within a range from about 0.1 to about 10, and wherein the molar ratio of total olefins to benzene falls within a range of about 0.5 to about 10.

43. A process as set forth in claim 42, further including obtaining said benzene-containing light hydrocarbon stream by: introducing a full boiling range benzene containing refinery stream into a distillation column to produce a bottoms fraction which is substantially benzene-free and said benzene-containing light hydrocarbon stream; and transferring said benzene-containing light hydrocarbon stream to said alkylation zone.

44. A process as set forth in claim 43, wherein the benzene content in the alkylated light hydrocarbon stream is reduced by at least 50%.

45. A process as set forth in claim 44, wherein the benzene content in the alkylated light hydrocarbon stream is reduced by at least 80%.

46. A process as set forth in claim 45, wherein the benzene-containing light hydrocarbon stream has from about 1 wt % to about 40 wt % benzene.

47. A process as set forth in claim 41, further including obtaining said benzene-containing light hydrocarbon stream by: introducing a full boiling range benzene containing refinery stream into a distillation column to produce a bottoms fraction which is substantially benzene-free and said benzene-containing light hydrocarbon stream; and transferring said benzene-containing light hydrocarbon stream to said alkylation zone.

48. A process as set forth in claim 47, wherein the benzene content in the alkylated light hydrocarbon stream is reduced by at least 50%.

49. A process as set forth in claim 48, wherein the benzene content in the alkylated light hydrocarbon stream is reduced by at least 80%.

50. A process as set forth in claim 49, wherein the benzene-containing light hydrocarbon stream has from about 1 wt % to about 40 wt % benzene.

51. A process as set forth in claim 34, wherein the alkylation zone is nondistilling.

52. A process as set forth in claim 34, wherein the alkylation zone is nondistilling.

53. A process as set forth in claim 35, wherein the olefin stream comprises an olefin-containing refinery stream containing 30 to 80 mole % propylene.

54. A process as set forth in claim 35, wherein the contacting step occurs in at least two catalyst beds and a portion of the olefin is added between the catalyst beds.

* * * * *

UNITED STATES PATENT AND TRADEMARK OFFICE
CERTIFICATE OF CORRECTION

PATENT NO. : 5,149,894
DATED : September 22, 1992
INVENTOR(S) : Dennis L. Holtermann and Robert A. Innes It is certified that error appears in the above-identified patent and that said Letters Patent is hereby corrected as shown below:

Col. 24, line 12, "benzene" should read --cumene--.

Col. 24, line 58, after "hydrocarbon" insert -- and $C_2$ to $C_4$ olefin into the first stage of an alkylator--.

Col. 26, line 14, "rang" should read --range--.

Col. 26, line 56, "nondistilling" should read --distilling--.

Signed and Sealed this

Ninth Day of November, 1993

Attest:

BRUCE LEHMAN

*Attesting Officer*   *Commissioner of Patents and Trademarks*